(12) United States Patent
Darian et al.

(10) Patent No.: US 8,353,912 B2
(45) Date of Patent: Jan. 15, 2013

(54) ULTRASONIC SPINAL SURGERY METHOD

(75) Inventors: Alexander L. Darian, Huntington Station, NJ (US); Dan Voic, Cedar Grove, NJ (US); Ronald R. Manna, Valley Stream, NY (US)

(73) Assignee: Misonix, Incorporated, Farmingdale, NY (US)

( * ) Notice: Subject to any disclaimer, the term of this patent is extended or adjusted under 35 U.S.C. 154(b) by 1171 days.

(21) Appl. No.: 11/809,676

(22) Filed: Jun. 1, 2007

(65) Prior Publication Data
US 2008/0300591 A1 Dec. 4, 2008

(51) Int. Cl.
*A61B 17/00* (2006.01)
(52) U.S. Cl. .......................... 606/84; 606/279
(58) Field of Classification Search ............ 204/157.15, 204/157.42, 157.62; 601/2; 606/79–80, 606/82–85, 86 R, 167–190, 279, 246, 86 A, 606/914; 623/17.11–17.16
See application file for complete search history.

(56) References Cited

U.S. PATENT DOCUMENTS

| | | | | |
|---|---|---|---|---|
| 5,484,398 A * | 1/1996 | Stoddard | .......................... | 604/22 |
| 5,976,105 A * | 11/1999 | Marcove et al. | .............. | 604/500 |
| 6,127,597 A * | 10/2000 | Beyar et al. | ................. | 606/86 R |
| 2002/0058944 A1* | 5/2002 | Michelson | ....................... | 606/79 |
| 2003/0195518 A1* | 10/2003 | Cragg | .............................. | 606/80 |
| 2005/0177184 A1* | 8/2005 | Easley | .......................... | 606/167 |
| 2006/0129160 A1* | 6/2006 | Liu et al. | ......................... | 606/85 |
| 2006/0149279 A1* | 7/2006 | Mathews | ........................ | 606/90 |
| 2006/0200155 A1* | 9/2006 | Harp | .............................. | 606/85 |

* cited by examiner

*Primary Examiner* — Andrew Yang
*Assistant Examiner* — Olivia C Chang
(74) *Attorney, Agent, or Firm* — R. Neil Sudol; Coleman Sudol Sapone P.C.

(57) ABSTRACT

In a discectomy method one removes at least a substantial portion of a spinal disc. Thereafter one operates an ultrasonic instrument to level opposing faces of vertebrae on opposite sides of the removed spinal disc. Graft or synthetic disc material is inserted between the vertebrae so that the graft or synthetic disc material is in contact with the leveled opposing faces. In an associated nucleotomy, a cannulated probe is inserted into a spinal disc and used to remove the nucleus pulposus. A synthetic or substitute nucleus material may then be inserted into the evacuated annulus.

5 Claims, 4 Drawing Sheets

ULTRASONIC SPINAL SURGERY METHOD

BACKGROUND OF THE INVENTION

This invention relates to surgical procedures commonly known as discectomy and nucleotomy.

The spinal column is comprised in part of bones or vertebrae and in part of fibrous discs that are disposed between the vertebrae. The discs normally function as cushions separating the vertebrae. With age, owing to a drying of the disks, the cushioning effect may be reduced. Also injury can cause a disc to bulge and press on the nerve root leaving the spinal column, possibly causing extreme pain.

More specifically, when the outer wall of a disc, called the annulus fibrosis, becomes weakened through age or injury, it may tear allowing the soft inner part of the disc, the nucleus pulposus, to bulge out. This is called disc herniation, disc prolapse, or a slipped or bulging disc. Once the inner disc material extends out past the regular margin of the outer disc wall, it can press against very sensitive nerve tissue in the spine. The "bulging" disc can compress or even damage the nerve tissue, and this can cause weakness, tingling, or pain in the back area and into one or both legs.

A discectomy is a surgical procedure generally to remove part of an intervertebral disc that is putting pressure on a nerve as it leaves the spinal column. The procedure is most commonly performed on lumbar discs (located in the lower back) creating leg pain. However, it may also be used for cervical discs in the neck.

Open discectomy is usually performed under general anesthesia (the patient is unconscious) and typically requires a one-day hospital stay. It is performed while the patient is lying face down or in a kneeling position. During the procedure, the surgeon will make an approximate one-inch incision in the skin over the affected area of the spine. Muscle tissue is removed from the bone above and below the affected disc and retractors hold the muscle and skin away from the surgical site so the surgeon has a clear view of the vertebrae and disc. In some cases bone and ligaments may have to be removed for the surgeon to be able to visualize and then gain access to the bulging disc without damaging the nerve tissue, this is called a laminectomy or laminotomy depending on how much bone is removed.

Once the surgeon can visualize the vertebrae, disc and other surrounding structures, he or she will remove the section of the disc that is protruding from the disc wall and any other disc fragments that may have been expelled from the disc. This is often done under magnification. No material is used to replace the disc tissue that is removed. The incision is then closed with sutures and the patient is taken to a recovery room.

The most common problem of a discectomy is that there is a chance that another fragment of disc will herniate and cause similar symptoms down the road. This is a so-called recurrent disc herniation, and the risk of this occurring is about 10-15%

OBJECTS OF THE INVENTION

It is an object of the present invention to provide an improved approach for a discectomy procedure.

It is a related object of the present invention to provide an improved procedure for a nucleotomy, the removal of a nucleus of a spinal disc.

Another object of the present invention is to provide a surgical discectomy method that is at least partially quicker and easier to carry out than conventional techniques.

A further object of the present invention is to provide a surgical discectomy method that includes the insertion of a graft or prosthetic disc between opposing vertebral bone surfaces.

A more particular object of the present invention is to provide such a discectomy method that enhances adhesion of the graft or prosthetic disc to opposing vertebral bone surfaces.

Yet another object of the present invention is to provide a surgical discectomy method that may be carried out in a minimally invasive procedure. These and other objects of the invention will be apparent from the drawings and descriptions herein. Although every object of the invention is attained in at least one embodiment of the invention, there is not necessarily any embodiment which attains all of the objects of the invention.

SUMMARY OF THE INVENTION

A surgical method comprises, in accordance with the present invention, inserting a distal end of an ultrasonic tool into a spinal disc between two vertebrae, generating a standing wave of ultrasonic frequency in the tool while the distal end of the tool is disposed in the spinal disc, thereby fragmenting a nucleus of the spinal disc, aspirating fragmented nucleus material from inside an annulus of the spinal disc, and removing the distal end of the tool from the annulus.

This method can be used in the performance of a nucleotomy. A synthetic material may be inserted into the annulus after the removal of the nucleus pulposus.

Pursuant to another feature of the present invention, the method further comprises removing the annulus from between the two vertebrae after the distal end of the tool has been removed and after at least a substantial portion of the nucleus of the spinal disc has been aspirated from the annulus. This extended method constitutes a discectomy.

After removal of the spinal disc, the two vertebrae may be fused to one another. Alternatively, a prosthetic disc or graft may be inserted between the two vertebrae. To implement the latter alternative, the present invention contemplates providing an ultrasonic probe having an operative head with at least one knurled lateral surface, contacting each opposing face of the vertebrae with a knurled lateral surface of the head after at least a portion of the annulus has been removed from between the two vertebrae, and ultrasonically vibrating the head during the contacting of each opposing face of the vertebrae, thereby leveling the opposing faces and providing the opposing faces with textured surfaces. The leveling and texturing of the vertebral surfaces opens access to the blood vessels in the vertebrae and facilitates subsequent growth and attachment of the bone to the material of a prosthetic disc or graft.

Pursuant to a more specific feature of the present invention, where the head of the ultrasonic probe is provided with at least two knurled planar surfaces, the contacting of each opposing face of the vertebrae includes contacting the opposing vertebral faces with respective knurled planar surfaces of the head. More specifically, the probe may take the form of an ultrasonic spatula probe, with knurled planar surfaces oriented parallel to a longitudinal axis of the spatula probe, and with the head having a thickness, measured between the opposing knurled planar surfaces, that is less than a distance between the opposing faces of the two vertebrae. In that case, the probe is manipulated to contact the opposing vertebral faces separately. Preferably, but not necessarily, the knurled surfaces of the probe head are at least nearly as wide as the opposing vertebral faces, so that the knurled surfaces need not be moved across the vertebral faces to ensure that the vertebral faces are leveled and textured in their entireties.

The probe may be provided with a channel for feeding a liquid to the knurled surfaces of the probe head during the contacting of the opposing faces of the vertebrae.

Where the ultrasonic probe has a distal end surface, the removing of the annulus may include contacting the annulus with the distal end surface of the probe, ultrasonically vibrating the head during the contacting of the annulus, thereby fragmenting at least a portion of the annulus, and removing the fragmented annulus from between the two vertebrae. The distal end face of the ultrasonic probe is much larger than the distal end of the ultrasonic tool or cannula, which facilitates removal of the annulus.

It is understood from the above description that the ultrasonic probe may be different from the ultrasonic tool. The tool may take the form of a cannula, optionally provided with a non-vibrating sheath for protecting overlying tissues of the patient during the procedure. The probe has a knurled lateral surface. Preferably, the knurled lateral surface is planar, for instance, where the probe is prismatic, triangular in cross-section, or in the form of a spatula.

Where the ultrasonic tool has a channel, the aspirating of the fragmented nucleus material may include suctioning the material through the channel. Typically, the channel extends longitudinally through the cannula. The inserting of the distal end of the tool into the spinal disc includes operating the tool to form an opening in the annulus of the spinal disc. Where the opening is formed on the anterior side of the annulus, the distal end of the tool is inserted into the spinal disc from an anterior side of a patient and the probe is likewise manipulated from the anterior side of the patient. Where the opening is formed on the posterior side of the annulus, the distal end of the tool is inserted into the spinal disc from a posterior side of a patient and concomitantly the probe is manipulated from the posterior side of the patient.

Irrigating fluid may be guided to the nucleus of the spinal disc after the inserting of the distal end of the ultrasonic tool into the disc.

A discectomy method comprises, in accordance with the present invention, operating a first ultrasonic surgical instrument to remove the entire nucleus pulposus and at least a substantial portion of the annulus fibrosis of a target spinal disc and subsequently operating a second ultrasonic surgical instrument to substantially remove the remaining annulus fibrosis of the spinal disc and to level opposing faces of the vertebral end plates. The second ultrasonic instrument may be different from the first ultrasonic instrument, in which case the first ultrasonic instrument is removed from the patient prior to inserting a distal end portion of the third ultrasonic instrument into the patient. The first ultrasonic instrument may take the form of a cannulated probe, while the second ultrasonic instrument has a knurled lateral surface oriented parallel to a longitudinal axis of the instrument.

After the removal of at least a substantial portion of the nucleus pulposus of the spinal disc and after at least partial removal of the annulus fibrosis of the spinal disc, and after leveling the vertebral end plates one may insert graft or synthetic disc material between the vertebrae so that the graft or synthetic disc material is in contact with the opposing faces.

A discectomy method in accordance with the present invention alternatively comprises removing at least a substantial portion of a spinal disc and thereafter operating an ultrasonic instrument to level opposing faces of vertebrae on opposite sides of the removed spinal disc. The ultrasonic instrument may be operated to provide the opposing vertebral faces with textured surfaces. Where the ultrasonic instrument has a head with at least one knurled surface oriented parallel to a longitudinal axis of the instrument, the leveling of either one of the opposing faces and the providing of a textured surface thereon includes bringing the knurled surface into contact with the one face and generating ultrasonic vibrations in the probe head during that contact. Where the probe head has two opposing knurled planar surfaces oriented parallel to the longitudinal axis, the leveling of the opposing faces and the providing of textured surfaces on the opposing faces including bringing the knurled planar surfaces into contact with respective ones of the opposing vertebral faces and generating ultrasonic vibrations in the probe head during the contacting of the knurled planar surfaces with the respective ones of the opposing vertebral faces. One may insert graft or synthetic disc material between the vertebrae, using conventional or standard surgical techniques, so that the graft or synthetic disc material is in contact with the leveled opposing faces. Alternatively, one could fuse (i.e., rigidly connect) the two vertebrae to one another, using standard surgical techniques.

In this alternative discectomy method in accordance with the present invention, the removing of the substantial portion of the spinal disc may be accomplished using a single ultrasonic tool such as a cannulated probe. In that case, the nucleus pulposus and at least a substantial portion of the annulus fibrosis are removed essentially simultaneously, during the same procedure. Alternatively, the nucleus pulposus may be removed first, separately from the annulus fibrosis. In that case, the removing of the substantial portion of the spinal disc may include inserting a distal end of an ultrasonic tool into the spinal disc, generating a standing wave of ultrasonic frequency in the tool while the distal end of the tool is disposed in the spinal disc, thereby fragmenting a nucleus of the spinal disc, and aspirating fragmented nucleus material from inside an annulus of the spinal disc. The removing of the spinal disc may further include bringing a distal end face of the ultrasonic tool or the ultrasonic instrument into contact with an annulus fibrosis of the spinal disc and generating ultrasonic vibrations in the tool or instrument during the contacting of the annulus fibrosis with the distal end face of the tool or instrument.

A particular embodiment of a surgical method comprises, in accordance with the present invention, (a) inserting a distal end of an ultrasonic tool into a spinal disc between two vertebrae, (b) generating a standing wave of ultrasonic frequency in the tool while the distal end of the tool is disposed in the spinal disc, thereby fragmenting a nucleus of the spinal disc, (c) aspirating fragmented nucleus material from inside an annulus of the spinal disc. Preferably the same tool is used to remove a majority of the annulus in a further step (d). The method additionally comprises (e) providing an ultrasonic spatula probe having a head with one or more knurled planar surfaces oriented parallel to a longitudinal axis of the spatula probe, the head having a distal end surface, (f) after the removing of a substantial portion of the annulus, contacting the remaining annulus with the distal end surface of the probe, (g) during the contacting of the annulus, ultrasonically vibrating the head, thereby fragmenting the remaining annulus, (h) removing the fragmented remaining annulus from between the two vertebrae, (i) contacting each opposing body end plate face of the vertebrae with a (there could be only a singular knurled surface) knurled planar surface of the probe, (j) during the contacting of the opposing vertebral body end plate faces, ultrasonically vibrating the head, thereby leveling the opposing vertebral body end plate faces and providing these opposing faces with textured surfaces, and (k) inserting graft or synthetic disc material between the vertebrae, using conventional or standard surgical techniques, so that the graft or synthetic disc material is in contact with the opposing vertebral faces.

Where the ultrasonic tool has a channel, the aspirating of the fragmented nucleus material may include suctioning the material through the channel. The tool may take the form of a cannula, with the channel extending longitudinally through the cannula. The inserting of the distal end of the tool into the spinal disc then includes operating the tool to form an opening in the annulus of the spinal disc.

The aspirating of the fragmented nucleus material may occur during the generating of the standing wave. Alternatively, the vibrating of the tool may be momentarily interrupted during the aspiration process.

The probe may be provided with a channel, enabling a feeding of an irrigation and cooling fluid through the channel during the contacting of the opposing faces of the vertebrae.

DETAILED DESCRIPTION

Figure 1:
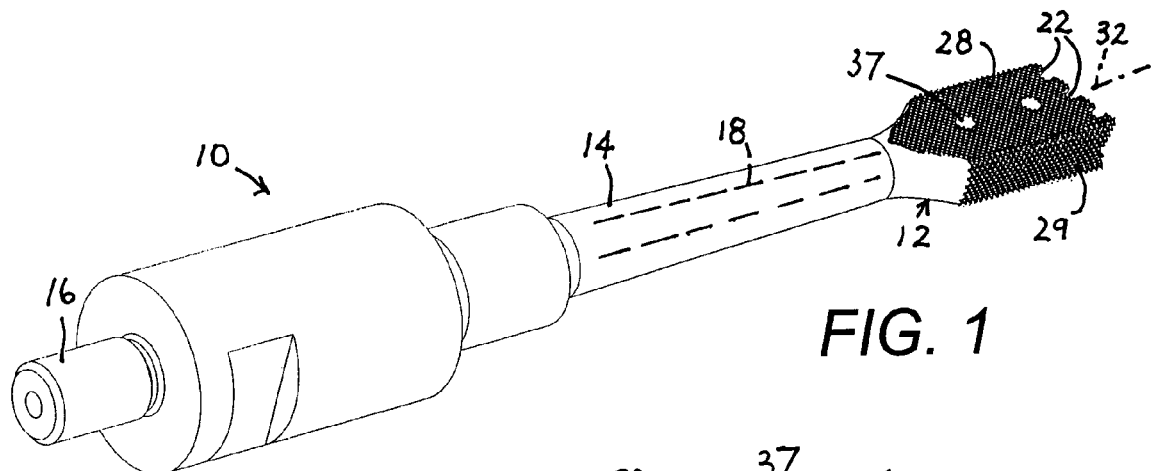
FIG. 1 is a schematic perspective view of an ultrasonic spatula probe for use in a discectomy method in accordance with the present invention.
Figure 2:
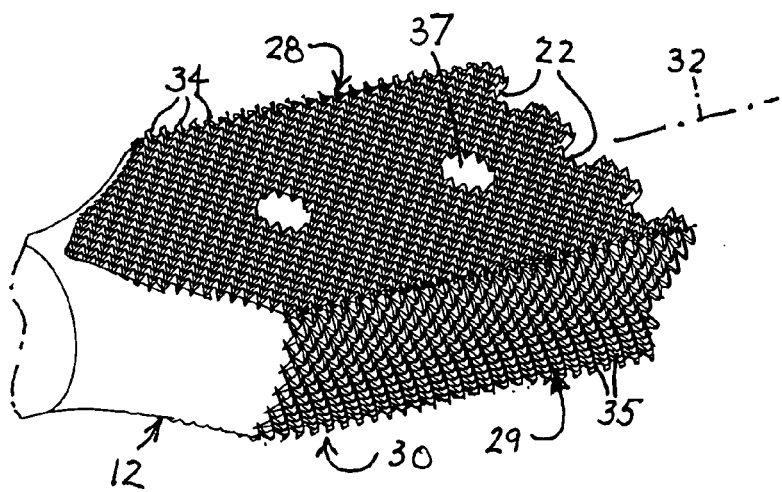
FIG. 2 is a schematic perspective view, on a larger scale, of a head of the spatula probe of FIG. 1.
Figure 3:
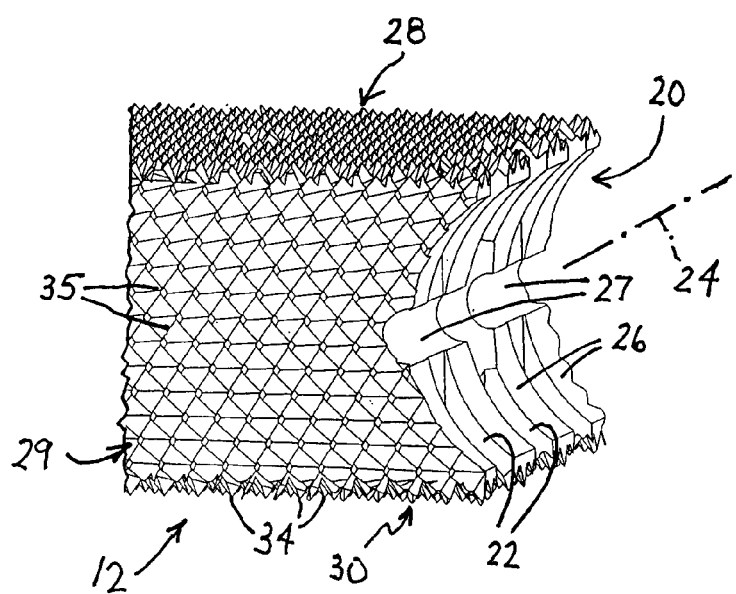
FIG. 3 is a schematic perspective view, on an even larger scale, of a distal end of the probe head shown in FIGS. 1 and 2.

FIGS. 1-3 depict an ultrasonic probe or instrument 10 with a transversely enlarged but flattened head 12 analogous to a spatula. Probe 10 is similar to probes disclosed in U.S. Patent Application Publication No. 2006/0241470 by Novak et al., the disclosure of which is hereby incorporated by reference.

Probe 10 includes a shaft 14 carrying head 12 at a distal end and provided at a proximal end with a connector 16 for coupling the probe to a piezoelectric or magnetostrictive transducer assembly such as that described and illustrated in U.S. Pat. No. 5,371,429 to Manna, the disclosure of which is hereby incorporated by reference. Shaft 14 is formed with a longitudinally extending channel 18 that may be used for conducting an irrigating and cooling liquid (e.g., saline solution, with or without medication) to a surgical site during use of the spatula probe 10.

As best seen in FIG. 3, head 12 is provided in a distal end face (not separately designated) with a channel, groove, indentation, or notch 20 occupying the entire width and 90% or more of the height of the probe head. Channel 20 has a cylindrical aspect owing to its formation by a rotary cutting blade (not shown). After the cutting of a substantially semi-cylindrical groove by the rotary blade, a machinist cuts a series of transverse notches 22 extending perpendicularly to an axis 24 of the groove. Channel 20 is thus defined by a series of cylindrical land areas or sections 26 separated from each other by notches 22.

Irrigation channel 18 extends to one or more notches 22 (as well as to one or more lateral faces of head 12) and thereby communicates with the transversely extending channel 20 in the end face of head 12. Channel 20 reduces the likelihood of blockage of an output opening (not shown) of the irrigation channel 18 by locating this opening or outlet proximally from the land surfaces or sections 26 of channel 20, while allowing the liquid to fill the channel 20 and cover the remaining distal surface area more fully. Another function of the notched or grooved structure of transverse end channel 20 is that notches 22 receive fragmented organic debris produced by the mechanical action of the distal end face of probe head 12, thereby increasing the ablation rate.

Many alternative shapes of channels may be employed in the distal end faces of ultrasonic probes without changing the concepts outlined herein and in U.S. Patent Application Publication No. 2006/0241470. Secondary channels 27 in addition to channel 18 may be incorporated in the distal end channel 20 to provide irrigation to the full width of the probe tip when tissue is fully engaged.

When irrigation channel 18 is connected to a suction source (not shown), fluid in the channel 18 flows toward connector 16 through channel 18. When the channel or bore 18 is connected to a source of irrigation liquid (not shown), liquid flows through channel 18 towards transverse end channel 20.

Probe head 12 is provided with a first pair of oppositely facing knurled lateral surfaces 28 and 30 and a second pair of oppositely facing knurled lateral surfaces 29 (only one visible in FIGS. 1-3) each generally parallel to a longitudinal axis 32 of probe 10. Knurled surfaces 28 and 30 are formed with a plethora of tiny teeth 34 that serve in part as energy guides or directors. Likewise knurled surfaces 29 are formed with a plethora of tiny pyramidal teeth 35 that serve in part as energy guides or directors. As discussed hereinafter, knurled surfaces 28 and 30 are used in a discectomy procedure to level opposing faces of adjacent vertebrae after removal of the associated disc from between the vertebrae. Teeth 34 and 35 have a fine geometrical configuration and distribution as one would find, for example, on a metal file. Alternative forms of knurling may be used, for instance, as described in U.S. Patent Application Publication No. 2006/0241470. Irrigation channels 37 may extend to lateral surfaces 28, 30 from main channel 18.

Figure 4:
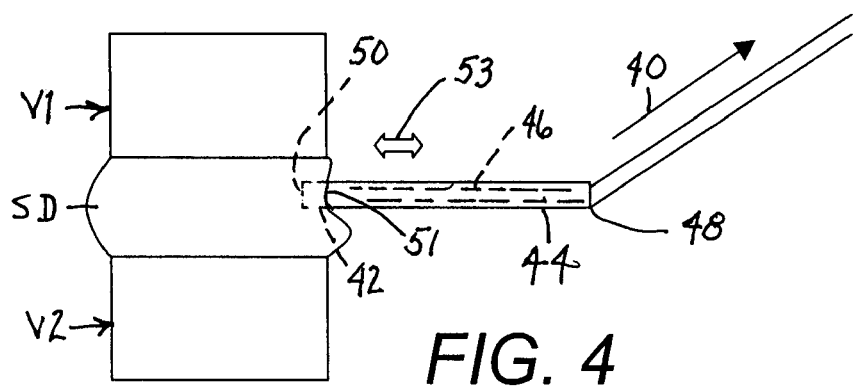
FIG. 4 is a schematic side elevational view of two vertebrae and a disc, showing a step in a nucleotomy or discectomy procedure in accordance with the present invention.
Figure 5:
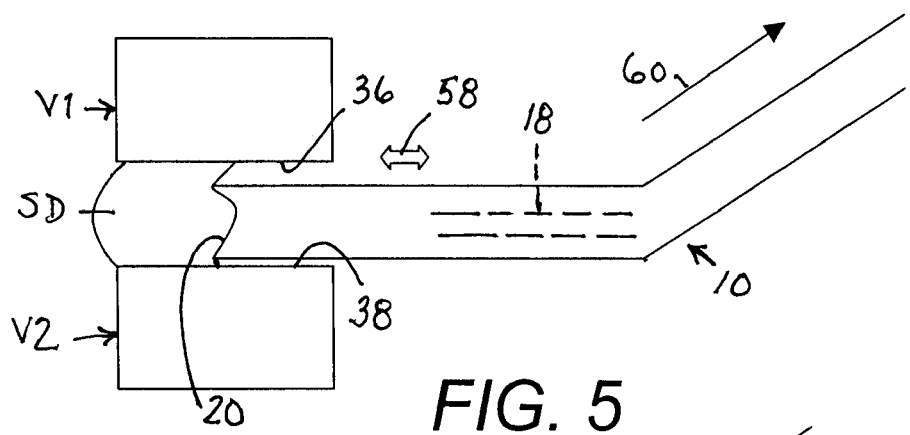
FIG. 5 is a schematic side elevational view of the two vertebrae of FIG. 4, showing a subsequent step in a discectomy procedure in accordance with the present invention.
Figure 6:
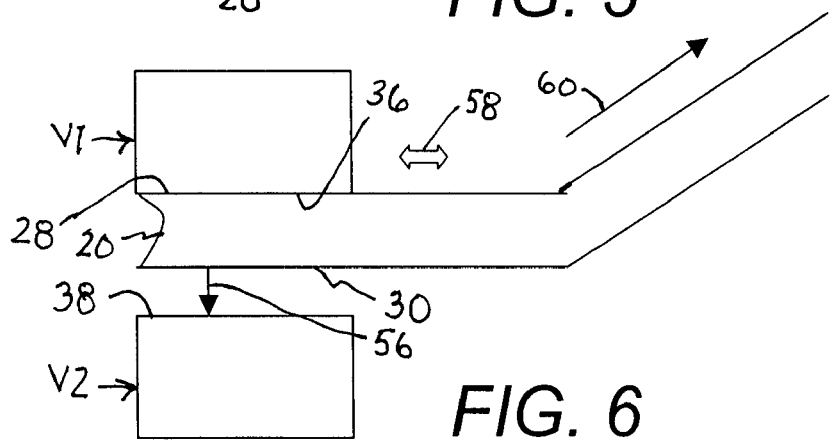
FIG. 6 is a schematic side elevational view of the two vertebrae of FIGS. 4 and 5, showing a further step in a discectomy procedure in accordance with the present invention.
Figure 7:
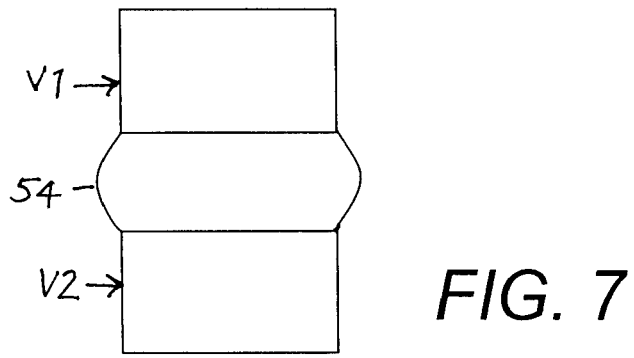
FIG. 7 is a schematic side elevational view of the two vertebrae of FIGS. 4-6, showing yet another step in a discectomy procedure in accordance with the present invention.

In the continuance of a discectomy method utilizing an ultrasonic probe 44 (FIG. 4), one removes at least a substantial portion of a spinal disc SD (FIGS. 4 and 5) and thereafter manipulates probe 10 to level opposing faces 36 and 38 of vertebrae V1 and V2 on opposite sides of the removed spinal disc SD (FIGS. 5 and 6). Subsequently, one inserts a prosthetic disc 54 made of graft or synthetic material between the vertebrae V1 and V2 so that the graft or synthetic disc material is in contact with the leveled opposing faces 36 and 38 (FIG. 7).

Owing to the knurled structure of probe surfaces 28 and 30, the use of probe 10 provides opposing vertebral faces 36 and 38 with textured surfaces. This opens access to the blood vessels in vertebrae V1 and V1 and facilitates subsequent growth and attachment of the bone to the material of prosthetic disc 54. More specifically, the use of probe 10 in this respect involves bringing a knurled planar surface 28 or 30 into contact with vertebra faces 36 and 38, respectively, and generating ultrasonic vibrations in the probe head 12 during that contact.

As depicted in FIG. 4, the removal of spinal disc SD is accomplished first by inserting a distal end portion 42 of ultrasonic tool 44 into the spinal disc from an anterior or posterior side thereof, transversely to the spinal column. Tool 44 is a cannula provided with a longitudinally extending channel 46. Tool 44 may have a bend 48 for facilitating access to the spinal disk SD when approach is made from the posterior side of the patient (patient lying on stomach). This approach and the entire operation may be conducted in a minimally invasive manner, i.e., laparoscopically.

A distal end face 50 of cannula 44 is pressed against the annulus fibrosis of disk SD and simultaneously a standing wave of ultrasonic frequency is generated in the cannula. The ultrasonic action of the cannula 44 creates an opening or perforation 51 in the annulus fibrosis. The operator or surgeon continues to push cannula 44 in the distal direction so that distal end 50 passes into the nucleus pulposus of the disk SD, as schematically represented in FIG. 4. Cannula 44 is manipulated from outside the patient and energized, with a standing compression wave 53 having an ultrasonic frequency, to fragment the material of the nucleus pulposus. During the entire procedure, suction 40 may be applied to channel 46 to aspirate tissue debris from disc SD. A strong vacuum may be required. The operator continues using cannula 44 until a substantial portion of the nucleus pulposus is extracted. Cannula 44 is then withdrawn from the patient.

The at least partially hollowed-out annulus fibrosis of the spinal disc SD is now at least sufficiently removed by the use of probe 10, as depicted in FIG. 5. More particularly, probe 10 is manipulated to move the distal end of head 12 transversely relative to the spinal column on an anterior or posterior side thereof and into engagement with the annulus fibrosis, while an ultrasonic standing mechanical pressure wave 58 is generated in the probe. During the contact of the probe end face, i.e., transverse channel 20, with the annulus fibrosis, an irrigation liquid may be fed to the surgical site via channel 18. The ultrasonic vibration of probe head 12 generates ultrasonic mechanical pressure waves in the annulus fibrosis and thereby disintegrates the annulus fibrosis, the fragments of which may be aspirated (arrow 60) through channel 18 or via an alternate suction path or instrument (not shown). The aspirating of the fragmented nucleus or annulus material may occur simultaneously or alternately with the fragmentation of the tissue.

After the removal of all or part of the annulus fibrosis, probe 10 is manipulated from outside the patient to place one knurled lateral surface 28 into contact with face 36 of vertebra V1, as depicted in FIG. 6. During this contact, probe 10 and particularly head 12 and surface 28 thereof are vibrated at an ultrasonic resonant frequency, pursuant to standard ultrasonic principles. The ultrasonic movement of knurled surface 28 against vertebral face 36 serves to level the vertebral face, open the bone to blood flow, and enhance the surface texture to promote bone growth and adhesion to a subsequently inserted prosthetic disk 54 (FIG. 7).

After the leveling and texturing of vertebral face 36, probe 10 is manipulated to move head 12 laterally, as indicated by an arrow 56 (FIG. 6) to place knurled surface 30 into contact with opposing vertebral face 38. During this contact, probe 10 and particularly head 12 and surface 30 thereof are vibrated at the afore-mentioned ultrasonic resonant frequency. Again, the ultrasonic movement of knurled surface 30 against vertebral face 38 levels the vertebral face, open the bone to blood flow, and enhance the surface texture to promote bone growth and adhesion to prosthetic disk 54.

Knurled probe surfaces 28 and 30 are preferably nearly as wide as the distance between surfaces 36 and 38 of vertebrae V1 and V2, so that faces 36 or 38 may be leveled and textured in their entireties by a single contact or application of the probe head 12. Probe head does not need to be laterally repositioned and again applied to the vertebral face 36 or 38 in order to treat an otherwise unaffected area of the vertebral face. The entire face is leveled and textured at once.

It is to be noted that transverse channel 20 occupies nearly the entire distal end of probe head 12 so that cylindrical land areas or sections 26 and notches 22 serve substantially as the distal end face of probe 10. The distal end face of probe 10 is much larger that the distal end of cannula 44, which facilitates removal of the annulus fibrosis.

It is to be noted further that the removal of the annulus fibrosis and the leveling of vertebral faces 36 and 38 may be accomplished by different instruments. However, the use of a single instrument, namely probe 10, is considered to be more efficient and efficacious.

Concomitantly, it within the scope of the present disclosure to effectuate the removal of the nucleus pulposus and the removal of the annulus fibrosis of spinal disk SD by a single ultrasonic instrument.

As indicated above, a discectomy operation using cannula 44 and probe 10 may be carried out from the anterior side of the patient. Such an operation may be conducted laparoscopically. Alternatively, the approach may be from the posterior side, with the patient, for example, in a kneeling position. The posterior approach may require ancillary equipment in the nature of bone cutting blades for effectuating an entry to the spine. A further ancillary instrument is an ultrasonic drill that may be used for forming holes in vertebrae V1 and V2 for receiving bone graft attachment screws (not shown).

In the posterior approach, the surgeon exposes posterior surfaces of the patient's spinal column in a desired area of treatment using standard or minimally invasive surgical techniques. Ultrasonic aspirators or ultrasonic scalpels may be used (in either the anterior or the posterior approach) for exposing the spinal disc in order to spare tissue and lower blood loss. The surgeon then uses an ultrasonic bone cutter to remove bone in large pieces to allow access to the target spinal disc SD. The remaining steps of the posterior approach are the same as in the anterior approach. The surgeon manipulates ultrasonic cannula tool 44 to perforate the disc SD into the nucleus thereof to debulk the disc. A high or strong vacuum may be needed. The surgeon continues the debulking the nucleus with cannula tool 44 until the nucleus is at least substantially removed and does not remove bone material from vertebral faces 36 and 38. The surgeon subsequently use ultrasonic spatula probe 10 to remove the remaining annulus from between vertebral bodies V1 and V2. Irrigation and aspiration may be used. Irrigation reduces heat and bone necrosis. Spatula side surfaces 28 and 30 are used to remove or level the vertebral endplates 36 and 38. Energy directors or teeth 34 or 35 may leave a textured surface, which is clinically desirable to allow knitting into bone graft or synthetic disc substitute. The surgeon inserts graft or synthetic disc material 54 as per standard surgical techniques. Drilling for bone graft screws is possible with an ultrasound aspirator and coring device (not shown).

Probe 10 may be manufactured in different sizes, i.e., with probe heads 12 of different thicknesses and different widths. Thus, surfaces 28 and 30 of different instruments may have different widths and different spacings. This variation is for purposes of facilitating a matching of the instruments to the particular spinal dimensions of different patients.

It is to be noted that removal of the nucleus pulposus through the use of cannula 44, as described hereinabove with reference to FIG. 4, constitutes a nucleotomy. In such a procedure as described herein, one exposes anterior or posterior surfaces of spinal disc SD in a desired area of treatment using standard surgical techniques. Ultrasonic aspirators or ultrasonic scalpels may be used for exposing the spinal disc SD in order to spare tissue and lower blood loss. One uses cannulated ultrasonic aspirator probe 44 to perforate the disc SD and penetrate into the nucleus pulposus to debulk the same. A high vacuum may be needed. Multiple perforation sites may be desired. One continues the debulking until desired amount of nucleus is removed and preserves all annulus fibrosis. Lowered ultrasound excursion and/or ultrasound power and/or vacuum levels may be instituted to improve tactile feedback and aid in preventing removal of annulus. A synthetic nucleus replacement may be inserted as per standard surgical technique. A small-diameter probe may be used such that the annulus fibrosis does not require any repair, depending on the method and materials used for replacing the nucleus pulposus. Blunt dissection of the annulus fibrosis may be used prior to introduction of the cannulated probe to provide access to the nucleus pulposus, thereby mitigating the need for repair of the annulus fibrosis after the nucleotomy is complete.

In yet another alternative procedure, vertebrae V1 and V2 may be fused or rigidly connected to one another.

Figure 8:
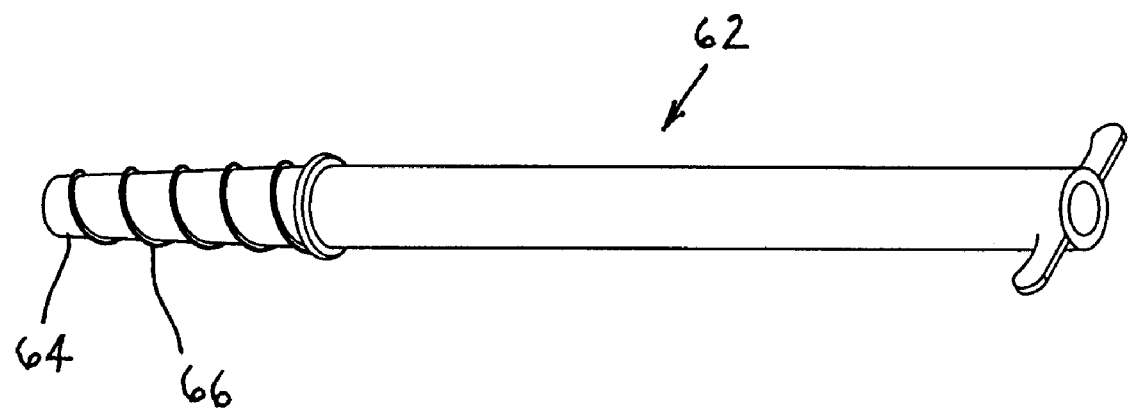
FIG. 8 is a schematic perspective view of an introducer sheath for use in a surgical nucleotomy or discectomy procedure in accordance with the present invention.
Figure 9:
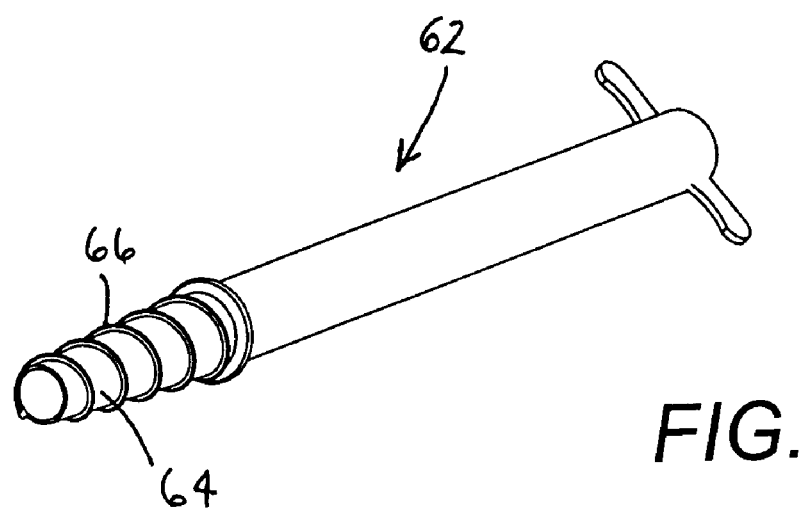
FIG. 9 is another schematic perspective view of the introducer sheath of FIG. 8.
Figure 10:
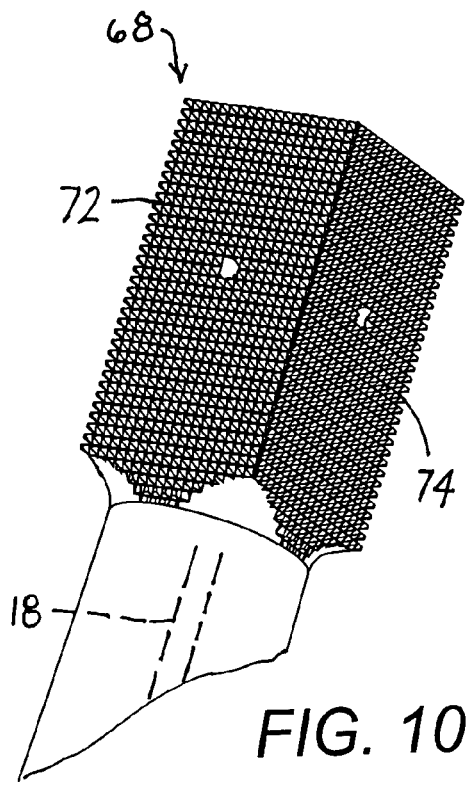
FIG. 10 is a schematic perspective view of another probe head for use in a discectomy procedure in accordance with the present invention.
Figure 11:
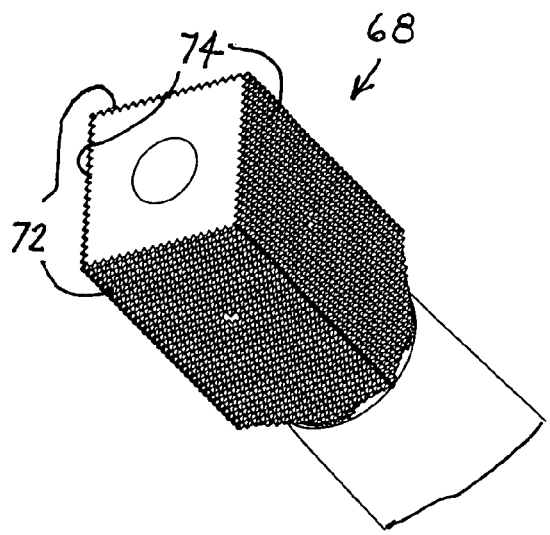
FIG. 11 is another schematic perspective view of the probe head of FIG. 10.
Figure 12:
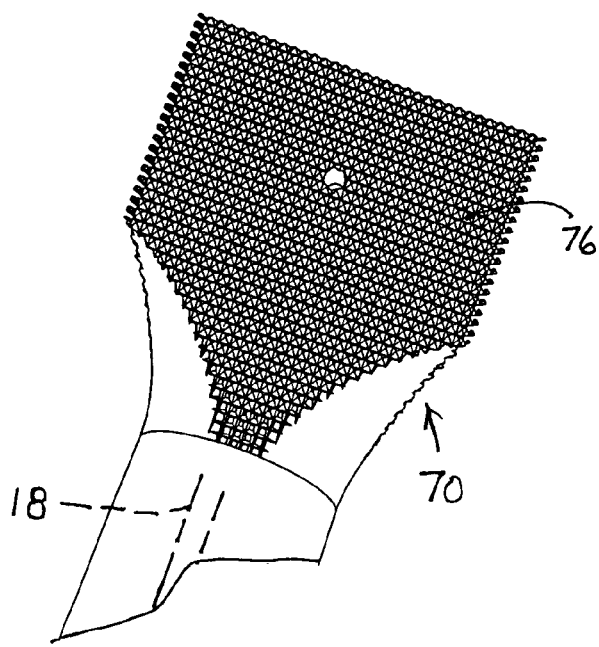
FIG. 12 is a schematic perspective view of yet another probe head for use in a discectomy procedure in accordance with the present invention.
Figure 13:
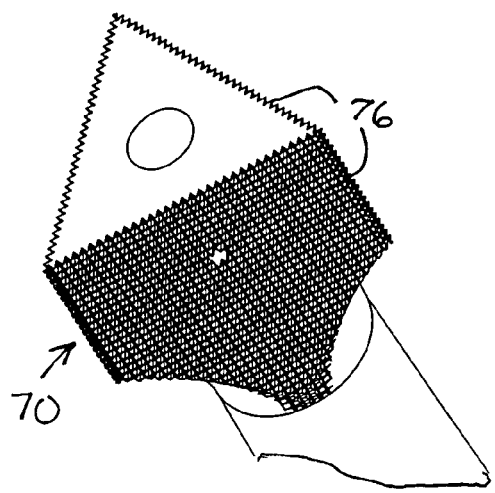
FIG. 13 is an additional schematic perspective view of the probe head of FIG. 12.

FIGS. 8 and 9 depict a rigid sheath 62 that may be used with cannula 44 or probe 10 to minimize heating and damage to surrounding tissue. Sheath 62 may also serve as an introducer device for perforating the annulus of a spinal disc SD. In that case, sheath 62 functions like a trocar, puncturing the annulus and having a cannulated cross section. A distal part 64, which punctures the annulus, may have one or more coarse external threads 66 to engage the annulus and hold the device in place. Sheath 62 allows the cannula 44 to be introduced and moved around without damaging the entry site of the annulus.

FIGS. 10-13 illustrated two other probe heads 68 and 70 that may be provided in an ultrasonic leveling and texturing discectomy probe. Probe head 68 is a right-rectangular prism with two pairs of opposed planar knurled lateral surfaces 72 and 74. Probe head 70 has a triangular cross-section with three planar knurled lateral surfaces 76. Other probe shapes may be used for hard tissue surface preparation, including heads a cylindrical cross-section. In any event, irrigation channel 18 has branches (not shown) extending to the knurled lateral surfaces 72, 74, 76 for purposes of controlling heat production at organic tissue surfaces.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A discectomy method comprising:
providing an ultrasonic instrument having a probe head with a longitudinal axis and a distal end face having a cylindrically concave profile, said probe head having a pair of lateral faces extending parallel to said axis, said lateral faces having knurled surfaces;
manipulating said ultrasonic instrument to insert said probe head into a spinal column of a patient, between adjacent vertebrae thereof;
with said distal end face in contact with an annulus fibrosis of the spinal disc, operating said ultrasonic surgical instrument to remove at least a substantial portion of the annulus fibrosis of said spinal disc; and
with one of said lateral end faces in contact with a first vertebral face of a respective one of said adjacent vertebrae, operating said ultrasonic instrument to level said vertebral face.

2. The method defined in claim 1, further comprising moving said ultrasonic instrument so that another of said lateral faces is in contact with a second vertebral face of the other of said adjacent vertebrae and operating said ultrasonic instrument to level said second vertebral face.

3. The method defined in claim 2 wherein said lateral faces of said probe head are parallel to one another.

4. The method defined in claim 1 wherein said cylindrically concave profile is a cylindrical channel, groove, indentation, or notch occupying a width of said probe head in its entirety and a substantial portion of a height of said probe head, said distal end face being further formed in said cylindrical channel, groove, indentation, or notch with a series of transverse notches extending perpendicularly to an axis of said cylindrical channel, groove, indentation, or notch, said cylindrical channel, groove, indentation, or notch being defined by a series of cylindrical land areas or sections separated from each other by said notches, the removing of the substantial portion of the annulus including:
inserting said probe head into said spinal disc between said adjacent vertebrae, said probe head being inserted into said spinal disc transversely to said spinal column from an anterior or posterior side thereof;
contacting the annulus with said cylindrical land areas or section of said distal end surface of said probe;
during the contacting of the annulus, ultrasonically vibrating said head, thereby fragmenting at least a portion of the annulus; and
removing the fragmented annulus from between the two vertebrae via said notches.

5. The method defined in claim 1 wherein said lateral faces of said probe head are contiguous with one another, further comprising operating said ultrasonic instrument with another of said lateral faces in contact with tissues of the patient.

* * * * *